United States Patent [19]

McGregor

[11] 4,087,431

[45] May 2, 1978

[54] PREPARATION OF 3,6-DICHLOROPICOLINIC ACID

[75] Inventor: Stanley D. McGregor, Midland, Mich.

[73] Assignee: The Dow Chemical Company, Midland, Mich.

[21] Appl. No.: 779,859

[22] Filed: Mar. 21, 1977

Related U.S. Application Data

[63] Continuation-in-part of Ser. No. 686,753, May 17, 1976, abandoned, which is a continuation-in-part of Ser. No. 536,789, Dec. 27, 1974, abandoned, and a continuation-in-part of Ser. No. 688,641, May 21, 1976, abandoned, which is a continuation-in-part of Ser. No. 536,788, Dec. 27, 1974, abandoned.

[51] Int. Cl.$^2$ .................. C07D 213/16; A61K 31/455
[52] U.S. Cl. ......................... 260/295 R; 260/295.5 R; 424/266
[58] Field of Search ..................... 260/295 R, 295.5 R

[56] References Cited

U.S. PATENT DOCUMENTS 3,971,799  7/1976  McGregor ....................... 260/295 R

OTHER PUBLICATIONS

Collins et al., J. of Chem. Soc. (c), Organic Chem., London 1971, pp. 167–174.

*Primary Examiner*—Henry R. Jiles
*Assistant Examiner*—Cary Owens
*Attorney, Agent, or Firm*—S. Preston Jones; C. Kenneth Bjork

[57] ABSTRACT

3,6-Dichloropicolinic acid is prepared by reacting 3,5,6-trichloro-4-hydrazino picolinic acid with from 2 to 3 moles of a basic reagent per mole of the picolinic acid reactant, acidifying the reaction mixture with a mineral acid and recovering the desired 3,6-dichloropicolinic acid product.

7 Claims, No Drawings

PREPARATION OF 3,6-DICHLOROPICOLINIC ACID

CROSS-REFERENCE TO RELATED APPLICATIONS

This application is a continuation-in-part of application Ser. No. 686,753 filed May 17, 1976 and now abandoned, which in turn is a continuation-in-part of application Ser. No. 536,789 filed Dec. 27, 1974, now abandoned. In addition, this application is a continuation-in-part of application Ser. No. 688,641 filed May 21, 1976 and now abandoned which in turn is a continuation-in-part of application Ser. No. 536,788 filed Dec. 27, 1974, and now abandoned.

BACKGROUND OF THE INVENTION 3,6-Dichloropicolinic acid is a crystalline solid melting at 150°–152° C useful as a pesticide and specifically adapted to be employed for the control of insects, mites, trash fish and microbes. The compound is also useful as a plant growth control agent. The compound, it use and method of preparation is taught in U.S. Pat. No. 3,317,549.

The 3,6-dichloropicolinic acid is taught in the above patent to be prepared by the acid hydrolysis of 3,6-dichloro-2-(trichloromethyl)pyridine. The 3,6-dichloro-2-(trichloromethyl)pyridine is mixed with either nitric, phosphoric or sulfuric acid and the mixture maintained for from ½ to 2 hours at 20° to 140° C.

While the above procedure gives high yields of the desired product, the overall process is very expensive due to the high production cost of the intermediate starting materials, thereby limiting the usefulness of the product. Processes are continually being sought employing more readily available and more economical starting material.

Collins et al, J. Chem. Soc., (c); pages 167–174 (1971) teach that halogens ortho and para to the ring nitrogen in pentachloropyridine are reactive with hydrazine hydrate. This reference further teaches the formation of tetrahalo-4-hydroxy pyridines from the action of aqueous sodium hydroxide on tetrahalo-4-hydrazinopyridines.

SUMMARY OF THE INVENTION

The present invention is directed to a process for the preparation of 3,6-dichloropicolinic acid. The process of the present invention comprises (a) reacting 3,5,6-trichloro-4-hydrazinopicolinic acid with from 2 to 3 moles of a basic reagent per mole of the picolinic acid reactant and (b) acidifying the reaction mixture with a mineral acid and recovering the desired 3,6-dichloropicolinic acid product.

The reactions which occur during the process of the present invention can be exemplified as follows.

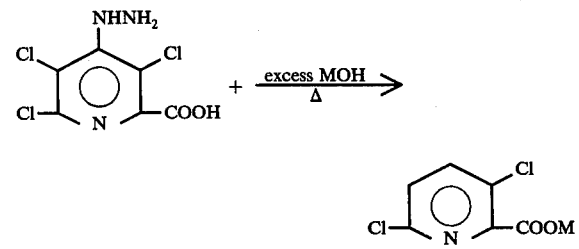

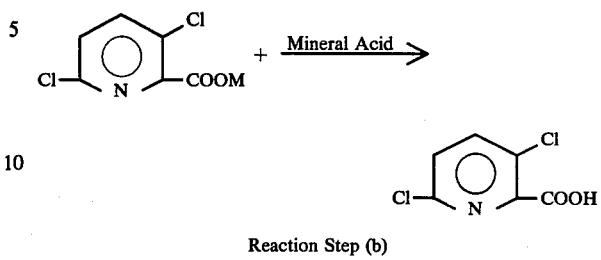

Reaction Step (b)

In the above exemplification of the reaction steps, M represents a base material from the group hereinafter set forth and no attempt has been made to present balanced equations.

In carrying out the process of the present invention, the 3,5,6-trichloro-4-hydrazinopicolinic acid is reacted with an excess of a base, with agitation, and heated at a temperature in the range of from about 60° to about 150° C or at the reflux temperature for about ½ hour to about 3 hours.

The base employed in carrying out this step, can be hydrazine itself or an alkali metal hydroxide in the form of an aqueous solution, a lower alkanol solution or an aqueous lower alkanol solution thereof. Representative lower alkanols include methanol, ethanol, propanol, isopropanol and butanol. Representative alkali metal hydroxides include sodium, potassium, cesium, lithium and rubidium hydroxides.

The 3,6-dichloropicolinic acid product, from the above step, in the form of the base salt, can be recovered as such by crystallization. In most cases it is more convenient to recover the product in the acid form. In such cases, the above reaction mixture is cooled and treated with a mineral acid employing conventional acid hydrolysis conditions. In order to insure complete conversion, acidification is usually carried to pH of about 1 to about 2 or less. The solid product can be separated by filtration or other conventional solid-liquid separatory procedures. If desired, the acid product can be further purified by washing with one or more of the following solvents such as water, methanol, ethanol, benzene and hexane or mixtures thereof.

PREPARATION OF STARTING MATERIALS

The 3,5,6-trichloro-4-hydrazinopicolinic acid can be prepared in a variety of ways. In one such method, tetrachloropicolinonitrile is reacted with hydrazine in the presence of a reaction medium and hydrogen chloride acceptor. The 3,5,6-trichloro-4-hydrazinopicolinonitrile product thus formed is reacted with an acid hydrolysis agent to prepare 3,5,6-trichloro-4-hydrazinopicolinic acid.

The reactions which occur during the above process can be exemplified as follows:

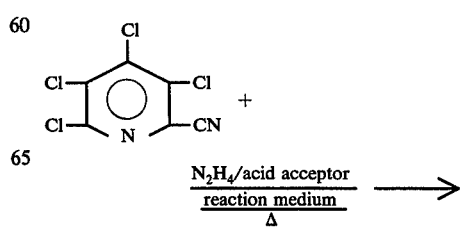

-continued

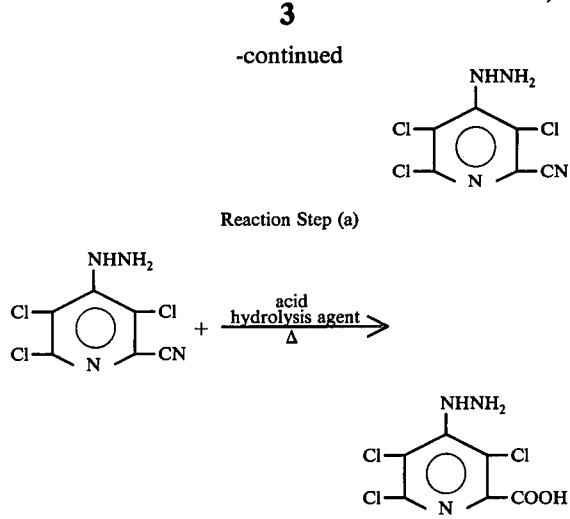

Reaction Step (a)

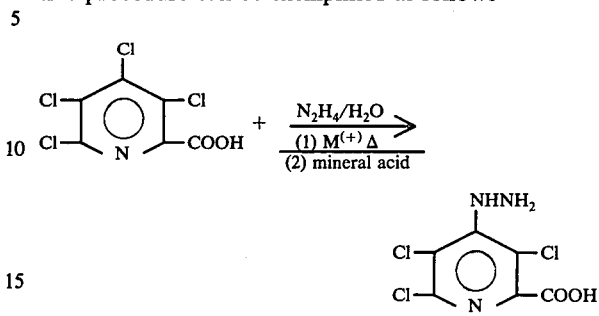

In the above exemplification of the reaction steps, no attempt has been made to present balanced equations.

In carrying out the above process step, the tetrachloropicolinonitrile is reacted with hydrazine in a reaction medium and in the presence of a hydrogen chloride acceptor at a temperature of from about 25° up to the reflux temperature for a period of from about 15 minutes to about 2 hours or more.

Representative reaction mediums include the lower alkanols, methanol, ethanol, propanol, isopropanol and butanol, tetrahydrofuran, dimethylformamide and pyridine.

Representative hydrogen chloride acceptors include among others, hydrazine, aliphatic tertiary amines, such as trimethylamine, triethylamine, tripropylamine and aromatic amines, such as dimethylaniline diethylaniline and pyridine.

The reaction consumes the reactants in stoichiometric proportions, however, in order to insure completion of the reaction, it is preferred that an excess of from about 5 to 100 percent of the hydrazine be employed. An additional excess of hydrazine will be necessary if hydrazine is employed as the hydrogen chloride acceptor.

At the completion of the reaction, the thus formed 3,5,6-trichloro-4-hydrazinopicolinonitrile intermediate can be separated if desired. If separation is desired, the reaction mixture is cooled and quenched with ice and/or cold water. The product which precipitates upon quenching can be separated by filtration, water washed and dried. If desired, the product can be further purified by recrystallization from a solvent such as benzene, or pyridine or mixtures thereof.

The 3,5,6-trichloro-4-hydrazinopicolinonitrile (separated or in situ) is reacted with an acid hydrolysis agent such as concentrated sulfuric acid solutions or concentrated hydrochloric acid. This reaction is carried out with agitation at a temperature of from about 80° C. to about 150° C. for a period of from about 30 minutes to about 2 hours. Thereafter, the reaction mixture is cooled and quenched by pouring over ice.

The 3,5,6-trichloro-4-hydrazinopicolinic acid product precipitates upon quenching and can be recovered by filtration or other conventional solid-liquid separatory procedures, washed with water and dried.

In an alternative preparative procedure, tetrachloropicolinic acid is reacted with hydrazine and a basic reagent in water followed by acidifying the above reaction product.

The reactions which occur during the above preparative procedure can be exemplified as follows wherein $M^{\oplus}$ represents the basic reagent as hereinafter defined. No attempt has been made to present a balanced equation.

In carrying out the above step, the tetrachloropicolinic acid, hydrazine and basic reagent are added to water, with agitation, and heated under reflux conditions for a period of from about 15 minutes to about 2 hours or more.

The reaction consumes the reactants in equalmolar proportions, however, in order to insure completion of the reaction, it is preferred that the base is present in an amount of from about 1 to about 2 moles for each mole of the tetrachloropicolinic acid and the hydrazine is present in an amount of from about 1 to about 2 moles for each mole of the tetrachloropicolinic acid.

Representative basic reagents which can be employed in carrying out this step include hydrazine, alkali metal hydroxides or carbonates such as, sodium, potassium, cesium, lithium and rubidium hydroxides or the corresponding carbonates. When hydrazine is employed as both a reactant and as the base, the hydrazine should be present in an amount of from about 3 to about 4 moles for each mole of the tetrachloropicolinic acid.

At the completion of this reaction, the thus formed 3,5,6-trichloro-4-hydrazinopicolinic acid:base salt intermediate can be separated if desired, or its conversion to the final product can be carried out in situ. If separation is desired and an alkali metal hydroxide was employed to convert the acid to the salt, the reaction mixture must have contained an additional molar equivalent of alkali metal hydroxide to remove the hydrogen chloride by-product. If on the other hand, an alkali metal carbonate was employed for the salt formation, the hydrazino intermediate can be immediately separated as the alkali metal bicarbonate by-product acts as a hydrogen chloride acceptor. If hydrazine itself was employed as set forth above, the excess over that necessary to form the 4-hydrazino derivative functions to form the hydrazide salt and also acts as the hydrogen chloride acceptor. If it is desired to convert the salt form of the compound to the acid form, such can be achieved by conventional practices of treating the salt with a mineral acid.

Representative mineral acids include, among others, hydrochloric acid, sulfuric acid and phosphoric acid.

DESCRIPTION OF SOME PREFERRED EMBODIMENTS

The following examples illustrate the present invention and the manner by which it can be practiced, but, as such, should not be construed as limitations upon the overall scope of the same.

EXAMPLE I

Preparation of 3,6-Dichloropropionic Acid

To a reaction flask containing 200 milliliters of water was added 26.1 grams (0.10 mole) of tetrachloropicolinic acid, 3.6 grams (0.11 mole) of hydrazine and 10.6 grams (0.1 mole) of sodium carbonate. The mixture was stirred and heated under reflux conditions for one and one half-hours.

To the above mixture was added dropwise over 15 minutes 6.0 grams (0.15 mole) of sodium hydroxide dissolved in 25 milliliters of water. The mixture was heated under reflux for one hour. The reaction mixture was cooled to 30° C and acidified with 10 milliliters of concentrated hydrochloric acid. The 3,6-dichloropicolinic acid product was collected by extracting the reaction mixture 3 times with 150 milliliter portions of methylene chloride, combining the extracts and removing the solvent by evaporation. The product was obtained in a yield of 14.9 grams (78 percent of theoretical) with a 3,6-dichloropicolinic acid purity of 90 percent.

EXAMPLE II

Preparation of 3,5,6-Trichloro-4-Hydrazinopicolinic Acid

To a reaction flask was added 26.1 grams (0.1 mole) of tetrachloropicolinic acid, 200 milliliters of water, 3.6 grams of 95 percent hydrazine (0.11 mole) and 10.6 grams (0.1 mole) of sodium carbonate. The mixture was heated with stirring and maintained under reflux conditions for about 1 hour. The reaction mixture was cooled to 25° C and 25 milliliters of 5 normal hydrochloric acid was added. The solid which precipitated was recovered by filtration, and washed successively with water, ethanol, benzene and hexane and air dried. The 3,5,6-trichloro-4-hydrazinopicolinic acid product was recovered in a yield of 25.6 grams (93 percent of theoretical) having a melting point of 165°–170° C. After recrystallization from a 50:50 dimethylformamide-water mixture the product (as the mono-hydrate) was found by analysis to have carbon, hydrogen and nitrogen contents of 26.6, 2.1 and 15.3 percent, respectively, as compared with the theoretical contents of 26.2, 2.2 and 15.3 percent, respectively, calculated for the above named compound.

EXAMPLE III

Preparation of 3,5,6-Trichloro-4-Hydrazinopicolinic Acid

To a reaction flask containing 200 milliliters of water at the boiling point was added 26.1 grams (0.1 mole) of tetrachloropicolinic acid, 4.1 grams (0.103 mole) of sodium hydroxide in 25 milliliters of water and 3.47 grams (0.105 mole) of hydrazine. The reaction mixture was stirred under reflux for 30 minutes. An additional 4.1 grams (0.103 mole) of sodium hydroxide in 25 milliliters of water was slowly added to the reaction mixture over a 25 minute period and the mixture refluxed for 45 minutes. The reaction mixture was cooled to room temperature and 25 milliliters of 5 Normal hydrochloric acid was added thereto. The solid 3,5,6-trichloro-4-hydrazinopicolinic acid (as the mono-hydrate), which precipitated was recovered by filtration in a yield of 22.9 grams (83.5 percent of theoretical) and melted at 166°–168° C.

EXAMPLE IV

Preparation of 3,6-Dichloropicolinic Acid

To a reaction flask containing 300 milliliters of each of water and ethanol under a nitrogen atmosphere was added 60 grams (0.23 mole) of 3,5,6-trichloro-4-hydrazinopicolinic acid. The mixture was heated to reflux and 60 milliliters of a 50 percent aqueous sodium hydroxide solution was added over 3 minutes. After an additional 45 minutes of heating under reflux, the reaction mixture was cooled to about 30° C and 100 milliliters of concentrated hydrochloric acid was added. The ethanol was removed from the reaction mixture by evaporation under reduced pressure and the solid 3,6-dichloropicolinic acid product was recovered by filtration and dried. The product was obtained in a yield of 23.5 grams (58 percent of theoretical) and was found by quantitative vapor phase chromatographic analysis to be 98.6 percent pure 3,6-dichloropicolinic acid.

The filtrate from the above filtration step was extracted 3 times with methylene chloride (portions equal to 150, 100 and 100 milliliters, respectively) and the combined extracts were dried over magnesium sulfate. The solvent was removed by evaporation leaving 11.8 grams of a solid which by analysis was found to be 70 percent pure 3,6-dichloropicolinic acid.

EXAMPLE V

Preparation of 3,6-Dichloropicolinic Acid

To a reaction flask containing 400 milliliters of water was added 30 grams (0.11 mole) of 3,5,6-trichloro-4-hydrazinopicolinic acid and 4.5 grams (0.11 mole) of sodium hydroxide dissolved in 25 milliliters of water. The reaction was heated to reflux and maintained under reflux while an additional 4.5 grams of sodium hydroxide dissolved in 25 milliliters of water was added dropwise over 50 minutes. The resulting solution was thereafter heated an additional 45 minutes under reflux and cooled to room temperature. The reaction mixture was mixed with 100 milliliters of methylene chloride and the solution acidified with 35 milliliters of concentrated hydrochloric acid. The two phases which formed were separated and the aqueous layer extracted twice with methylene chloride. The extracts were combined and dried over magnesium sulfate and the solvent evaporated to give 13.1 grams (62 percent of theoretical) of 3,6-dichloropicolinic acid.

EXAMPLE VI

Preparation of 3,5,6-trichloro-4-hydrazinopicolinonitrile

To a reaction flask was added 400 milliliters of 95 percent ethanol and 24.2 grams (0.10 mole) of tetrachloropicolinonitrile. The mixture was heated to 45° C. with stirring and 3.7 grams (0.11 mole) of 95 percent hydrazine and 10.1 grams (0.10 mole) of triethylamine was added thereto. The mixture was heated under reflux for 1 hour and the reaction mixture thereafter cooled to 40° C. To this mixture was added 400 grams of an ice-water mixture and the solid 3,5,6-trichloro-4-hydrazinopicolinonitrile product which precipitated was recovered by filtration, water washed and dried. The product was recovered in a yield of 20.6 grams (87 percent of theoretical) melting at 178°–181° C.

In another operation carried out essentially as above but employing tetrahydrofuran as the reaction medium the 3,5,6-trichloro-4-hydrazinopicolinonitrile product was recovered in a yield of 63 percent of theoretical and the product melted at 166°–179° C.

EXAMPLE VII

Preparation of 3,5,6-trichloro-4-hydrazinopicolinic Acid.

To a reaction vessel containing 50 milliliters of water and 200 milliliters of concentrated sulfuric acid was slowly added, with agitation, 50 grams (0.2 mole) of 3,5,6-trichloro-4-hydrazinopicolinonitrile. The mixture was heated for 1 hour at 115°–120° C. and the mixture cooled to 50° C. and poured over ice. The solid 3,5,6-trichloro-4-hydrazinopicolinic acid which precipitated was recovered by filtration, water washed and successively washed with methanol, benzene and hexane. The product (as the sulfate salt) was obtained in a yield of 54 grams (88 percent of theoretical) melting at 206°–207° C.

What is claimed is:

1. A process for preparing 3,6-dichloropicolinic acid which comprises:
   (a) reacting 3,5,6-trichloro-4-hydrazinopicolinic acid with from 2 to 3 moles of a basic reagent per mole of the picolinic acid reactant at a temperature of from about 60° C to the reflux temperature for about one-half hour to about three hours; and
   (b) acidifying the reaction mixture to a pH of about 1 with a mineral acid and recovering the desired 3,6-dichloropicolinic acid product.

2. The process as defined in claim 1 wherein the basic reagent is hydrazine.

3. The process as defined in claim 1 wherein the basic reagent is an aqueous alkali metal hydroxide solution.

4. The process as defined in claim 1 wherein the basic reagent is an aqueous lower alkanol/alkali metal hydroxide solution.

5. The process as defined in claim 4 wherein the aqueous lower alkanol/alkali metal hydroxide solution is an aqueous ethanol/sodium hydroxide solution.

6. The process as defined in claim 1 including the step of preparing 3,5,6-trichloro-4-hydrazinopicolinic acid which comprises reacting under reflux conditions for a period of from about 15 minutes to about 2 hours, tetrachloropicolinic acid with from about 1 to about 2 moles of each of hydrazine and a basic reagent.

7. The process as defined in claim 1 including the step of preparing 3,5,6-trichloro-4-hydrazinopicolinic acid which comprises
   (a) reacting at a temperature of from about 25° to the reflux temperature for a period of from about 15 minutes to about 2 hours, tetrachloropicolinonitrile with about a 5 to 100 percent stoichiometric excess of hydrazine in a reaction medium and a hydrogen chloride acceptor and
   (b) reacting the thus formed 3,5,6-trichloro-4-hydrazinopicolinonitrile intermediate with an acid hydrolysis agent, for a period of from about 30 minutes to about 2 hours at a temperature of from about 80° C to about 150° C.

* * * * *

UNITED STATES PATENT AND TRADEMARK OFFICE
CERTIFICATE OF CORRECTION

PATENT NO. : 4,087,431

DATED : May 2, 1978

INVENTOR(S) : Stanley D. McGregor

It is certified that error appears in the above—identified patent and that said Letters Patent are hereby corrected as shown below:

Column 1, line 22 "The compound, it use and" should read
-- The compound, its use and --;

Column 5, line 10 "one half-hours" should read --
one-half hours --.

Signed and Sealed this

Tenth Day of October 1978

[SEAL]

Attest:

RUTH C. MASON
Attesting Officer

DONALD W. BANNER
Commissioner of Patents and Trademarks